(12) United States Patent
Hughes

(10) Patent No.: US 6,554,792 B2
(45) Date of Patent: Apr. 29, 2003

(54) SUSPENSION DEVICE AND METHOD

(75) Inventor: Michael Scott Hughes, Glencoe, MO (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/316,315

(22) Filed: May 21, 1999

(65) Prior Publication Data

US 2001/0018571 A1 Aug. 30, 2001

(51) Int. Cl.⁷ .............................................. A61M 37/00
(52) U.S. Cl. ..................... 604/85; 604/218; 222/386; 222/145.1; 600/420; 600/432
(58) Field of Search .................... 604/82–85, 92, 604/93.01, 131, 140, 150, 87, 181, 183, 187, 218; 222/145.1, 145.5, 326, 386; 424/9.5, 9.52; 600/300, 407, 410, 419, 420, 437, 458, 427, 431–432

(56) References Cited

U.S. PATENT DOCUMENTS

| | | | |
|---|---|---|---|
| 964,730 A | * | 7/1910 | Ackerman |
| 1,428,043 A | | 9/1922 | Lyons |
| 3,373,906 A | | 3/1968 | De Hart et al. ............. 222/235 |
| 3,378,168 A | | 4/1968 | Hildebrandt ................ 222/83 |
| 3,464,412 A | | 9/1969 | Schwartz .................... 128/218 |
| 3,760,806 A | * | 9/1973 | Leeper |
| 3,858,853 A | | 1/1975 | Rausch et al. ................ 259/40 |
| 4,147,621 A | | 4/1979 | Giddings ..................... 210/22 |
| 4,596,555 A | | 6/1986 | Theeuwes .................... 604/56 |
| 4,776,704 A | | 10/1988 | Kopunek et al. ............. 366/184 |
| 4,941,751 A | | 7/1990 | Mühlbauer ................... 366/176 |
| 5,030,203 A | | 7/1991 | Wolf, Jr. et al. ............. 604/85 |
| 5,053,019 A | * | 10/1991 | Duffy ............................ 600/4 |
| 5,071,040 A | | 12/1991 | Laptewicz, Jr. ............. 222/235 |
| 5,246,670 A | | 9/1993 | Haber et al. ................ 422/102 |
| 5,286,257 A | | 2/1994 | Fischer ....................... 604/82 |
| 5,318,539 A | | 6/1994 | O'Neil ........................ 604/118 |
| 5,330,426 A | * | 7/1994 | Kriesel et al. |
| 5,352,036 A | | 10/1994 | Haber et al. ................ 366/130 |
| 5,395,323 A | | 3/1995 | Berglund ..................... 604/84 |
| 5,716,339 A | | 2/1998 | Tanaka et al. ................ 604/82 |
| 5,725,500 A | | 3/1998 | Micheler ..................... 604/82 |
| 5,806,519 A | | 9/1998 | Evans, III et al. .......... 128/654 |
| 5,891,087 A | | 4/1999 | Ohtani et al. ................ 604/89 |
| 5,897,530 A | * | 4/1999 | Jackson |
| 6,033,645 A | | 3/2000 | Unger ......................... 424/9.5 |
| 6,177,061 B1 | * | 1/2001 | Klaveness et al. |

FOREIGN PATENT DOCUMENTS

| | | | |
|---|---|---|---|
| EP | 0664136 | 7/1995 | ............ A61M/5/28 |
| WO | WO9608227 | 3/1996 | |

* cited by examiner

Primary Examiner—Brian L. Casler
Assistant Examiner—LoAn H. Thanh
(74) Attorney, Agent, or Firm—Wood, Herron & Evans, L.L.P.

(57) ABSTRACT

A device and method for providing a suspended agent such as a contrast agent without mechanical resuspension. A volume of agent is divided into sub-volumes in a network of tubes, cells, sponges, grooves, etc. A propellant fluid flows through the network to release the suspended agent. The network may be internal to a container for the propellant fluid. Alternatively, the network may be adjacent an exit port of a container for the propellant fluid, or may be in-line between a propellant fluid container and a patient. The invention reduces sedimentation of agents into one or a few aggregates and eliminates a mechanical mixing step. The invention thus provides a uniformly suspended agent, improving patient health and safety and increasing cost and time savings.

7 Claims, 3 Drawing Sheets

SUSPENSION DEVICE AND METHOD

FIELD OF THE INVENTION

Figure 1:
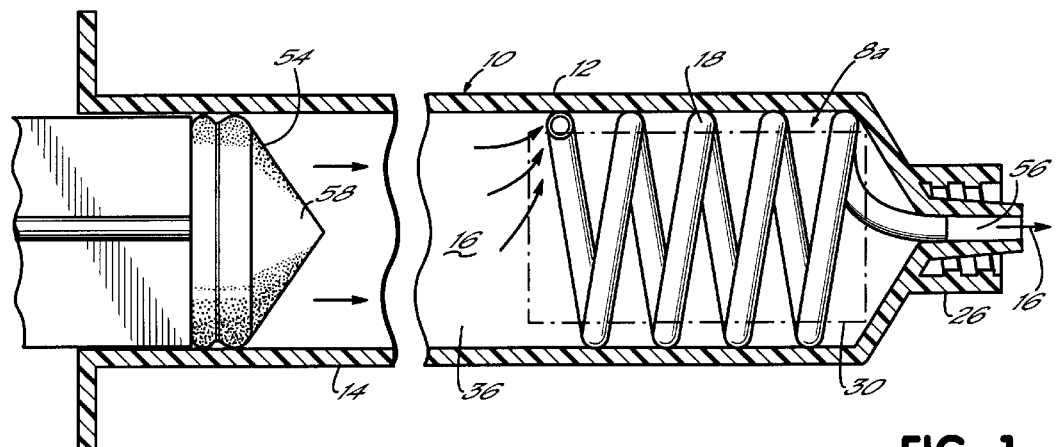
Figure 1A:
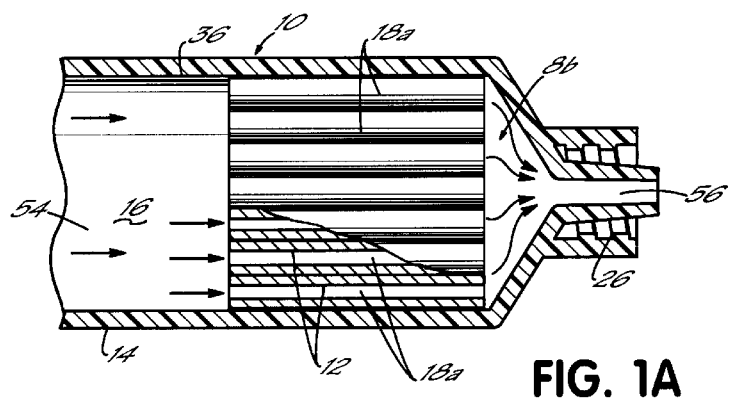

The invention relates to a device and method of using the device for providing a suspended volume of an agent without additional mixing.

BACKGROUND

Agents that do not persist in a suspended state and sediment must be resuspended prior to use. One example of an agent that must be resuspended prior to use is a pharmaceutical colloid, such as a contrast agent that is injected into a patient to enhance an imaging procedure. Contrast agents are used in various types of imaging including x-ray, magnetic resonance imaging (MRI), computed tomography (CT) and ultrasound (US). A contrast agent that comes out of suspension must be resuspended before placing the desired volume to be dosed into a delivery container such as a syringe. If there is a delay before the dose is injected into a patient, for example while preparing the patient or equipment, or if the infusion is extended, the agent must again be suspended before or during administration.

Resuspension of contrast agent requires mechanical manipulations, for example, removing a filled syringe positioned in an injector and remixing its contents. Additional remixing steps may delay a critical infusion time or, if remixing is omitted, the entire imaging procedure may have to be repeated due to suboptimal contrast obtained. Duplicate procedures not only put patients at increased risk and inconvenience, but are also cost- and time-inefficient. Even if the need to resuspend a single bolus injection is not prohibitive for a given procedure, repeated bolus injections or long term continuous infusions can become problematic due to agent coming out of suspension during administration.

The loss of suspension for a contrast agent at any point in a delivery system to a patient, such as in a syringe and/or in the connecting tubing, severely limits the duration of continuous infusions or the time between intermittent injections. The need to initially resuspend the colloid or other type of agent, and to further suspend if the agent is not used shortly after resuspension, requires either time-consuming effort and vigilance by the user or the use of mechanical mixing devices. In any case, the need to resuspend an agent poses an additional step and a possible source of error in an imaging procedure.

SUMMARY OF THE INVENTION

The invention is directed to a device that provides a suspended agent without additional mechanical mixing. The device divides a total volume of a sedimenting agent into a network of sub-volumes and has ports for an inflow and outflow of a propellant fluid to release the sub-volumes of agent from the device. In one embodiment, the device is located within a container in which the agent is packaged, such as a vial or bottle, or in a container in which the agent is dosed, such as a syringe or bag, or in a container containing the propellant fluid. In another embodiment, the device is located external to a container for the propellant fluid. In this embodiment, the device may be operably attached to an exit port of the propellant fluid container. Alternatively, in this embodiment, the device may be positioned in-line at any point with lines that connect the propellant fluid container with a patient connector. The device is comprised of a network of sub-volumes that may take the form of one or more tubes, cells and/or sponges, and that may assume any configuration such as a parallel, stairstep, helical, random and/or coiled configuration. The network may be retained in a network holder.

The invention is also directed to a suspension device for a volume of an agent in which a container for the propellant fluid has a network of grooves that are integral with the container and that retain a sub-volume of the agent within the grooves. The container has a plug that occupies an internal volume of the container and the grooves are either integral with an internal wall of the container, or are integral with an external wall of the plug. In either embodiment, the plug diverts the propellant fluid flow to a variable extent from the center of the container to the periphery of the container, thus diverting fluid flow through the grooves. The grooves may further contain substantially perpendicular channels at regular intervals to allow uniform filling of the grooves with the agent.

The invention is also directed to a method of providing a volume of suspended agent to a patient. The method includes dividing the volume of agent into contained sub-volumes, storing the sub-volumes in a network for containing sub-volumes of the agent and providing a propellant fluid under pressure to eject the sub-volumes of agent through the network and into a patient. The propellant fluid may be housed in a container in which the network is also located. Alternatively, the network may be external to the propellant fluid container, with the network positioned either in-line between a source of propellant fluid and a patient, or adjacent an exit port of a propellant fluid container.

The invention is also directed to a suspension device for a volume of an imaging contrast agent. A network contains a plurality of sub-volumes of the agent and has inflow and outflow ports for propellant fluid. The device may also have a container and network holder external to the container.

The objectives and other advantages of this invention will be further understood with reference to the following drawings and detailed description.

BRIEF DESCRIPTION OF THE FIGURES

FIG. 1 is a cross-sectional view of a syringe container with an internal tubular network.

FIG. 1A is a view similar to FIG. 1 of an alternate embodiment of the invention.

FIG. 2 is a cross-sectional view of a syringe container with an external tubular network operably attached to a propellant fluid container exit port.

FIG. 3 is an elevational view of an in-line device.

FIGS. 4A, 4B and 4C are various network embodiments and configurations.

FIG. 5 is a cross-sectional view of a syringe container having an integral network.

FIG. 6 is a cross-sectional view of an integral network with channels.

DETAILED DESCRIPTION

The device of the invention sub-divides a desired volume of an agent to suspend the agent without mechanical mixing. Resuspension is caused by viscous fluid flow through the network of sub-volumes. As used herein, the device is comprised of a network of structures for containing sub-volumes of the agent, with the entire volume of agent contained in the network component sub-volumes. As will be described, the device may be located in the same container that contains propellant fluid to eject the agent from the network (container package embodiment). Alternatively, the device may be located adjacent an exit port of a propellant fluid container (add-on embodiment), or may be positioned in-line at any point in a fluid path between the propellant fluid container and the ultimate deposit site such as a patient (in-line embodiment). As used herein, a propellant fluid is one that is used to eject the agent from the network of tubes, cells, etc. As used herein, a network is defined as a collection of structures which contain the entire desired volume of agent in sub-volumes, and hence increase the surface area of the agent over which the propellant fluid must flow, in the device. In one embodiment, the network has a common exit port, and agent sub-volumes are ejected from the network at a substantially equal rate. The network may encompass tubes, cells, sponges, etc. and is not limited by volume or configuration.

The device sub-divides a volume of an agent to prevent it from settling or sedimenting into one or a few dense aggregates without the need for mechanical mixing or suspending prior to use, and thus reduces or eliminates the problem of remixing or resuspending an agent that has come out of suspension prior to use. Use may be either preparing an injection dose by transferring the desired volume of agent from a package to a dosing container such as syringe, or injecting the dosing volume of agent into a patient. This problem may occur with contrast agents, either while in their package or portioned in a container such as a syringe for injecting into a patient about to undergo an imaging procedure. The invention solves the problem by subdividing the volume of the agent to prevent separation or aggregation of the agent from the suspending liquid.

Dividing a uniformly suspended contrast agent or other agent into a network of sub-volumes rather than a single large volume inhibits the particles from either floating or precipitating into one or more larger masses or aggregates. The invention thus reduces or obviates the need for mixing before or during a process, such as an infusion process. This increases the quality, safety, and cost- and time-efficiencies of the process.

With reference to FIG. 1, a network **8*a* containing divided sub-volumes of an agent 12 is internal to a container 10 for propellant fluid 16. The container 10 may be a syringe 14 or other types of containers which include but are not limited to vials, bags having flexible or semi-flexible walls, bottles of either glass or plastic, etc. The agent 12 contained in the network 8*a* is ejected from the container 10 as propellant fluid 16 flows through the network 8*a* and displaces the agent 12. The propellant fluid 16 is any viscous fluid (liquid or gas) that is biocompatible. The propellant fluid may be a diluent for the agent 12 such as normal saline, water, buffer, etc. The propellant fluid 16 may also be a contrast agent that is different from the agent 12** injected for the imminent imaging procedure.

The network **8*a* may be any structure that serves to contain a sub-volume of the desired total volume of an agent 12 in a unit area. The network 8*a* may be contained in a network holder 22. The network 8*a* may be tubes 18 which, as used herein, encompass tubules, microtubules, channels, or other types of hollow cylinders that convey a fluid or that function as a passageway, whereby a volume of agent 12 is divided into sub-volumes of any size. There are numerous configurations of the tubes 18 that can be used to sub-divide the volume of agent 12. These include, but are not limited to, a single long tube 18 as best shown in FIG. 1 or a collection of tubes 18*a* as shown in FIG. 1A. The tubes 18 may be in any configuration, such as one or more coils or helices, an angular or stairstep configuration, and/or even random configurations. A collection of tubes 18 may similarly be one or more coils or helices, an angular or stairstep configuration, and/or even random configurations, or may be arranged in a parallel configuration (FIG. 1A). The geometries and configurations of the network 8 may be combined in either regular or random configurations. While FIGS. 1 and 1A show tubes 18 positioned in a syringe 14 without any accompanying support, other configurations are contemplated. For example, the tubes 18 may be positioned within a network holder 22 (FIGS. 2 and 3), or may be supported or held in a syringe 14 or network holder 22 by a fixture such as 30 (shown in phantom lines in FIG. 1) which may extend for part of or all of the length of the network 8**.

With reference to FIG. 2, a dose delivery container 10 that is a syringe 14 is shown with a network holder 22 containing the network 8 external to the syringe 14. The network **8*c* is packaged within a network holder 22, which may be any container in which the network is housed or retained and may be made of any biocompatable material. The network holder 22 containing the network 8*c* may be separable from the syringe 14 or other container 10 and attached to an exit port 24 of the syringe 14 or container 10. The network holder 22 for the network 8*c* may also be manufactured as part of the container 10, which may be useful as a pre-packaged embodiment of the invention. In a non-pre-packaged embodiment, the network holder 22 may be attached to an exit port 24 using, for example, connectors 26 such as luer fittings. The exit port 24 of the syringe 14 may be fitted with luer fittings, such as Luer-Lok® caps (Becton-Dickinson), or may have luer fittings such as metal, brass or glass luer tips attached. As previously described, a support or fixture 30 for the tubes 28 may be used, and the support 30 and tubes 28 may be contained in a network holder 22. As one alternative, the support 30 and tubes 28 may be contained directly in the container 10. As another alternative, the tubes 28 in a network holder 22 may be unsupported as shown in FIG. 2**.

While FIG. 2 illustrates a network holder 22 which is attached to a syringe 14, other embodiments are contemplated. With reference to FIG. 3, the network (not shown) contained in a network holder 22 is shown in an in-line embodiment. The network holder 22 is fashioned with connectors 26 at both an inflow port 32 and an outflow port 34. Tubing is connected to connectors 26 to carry propellant fluid 16 from a syringe to holder 22 and from holder 22 to a patient. The connectors 26 may be the same or different at the inflow 32 and outflow 34 ports and may be any type such as luer fittings, as previously described. Network holder 22 and the network inside may be configured symmetrically, so that the orientation of the network holder 22 in an in-flow embodiment need not be a concern; i.e., there is no back-to-front or front-to-back limitation. Agent 12 can be removed from the network within the network holder 22 upon pressure from a propellant fluid 16.

A network 8 that is internal to a container 10 such as a syringe 14 need not be housed in a network holder 22. As seen in FIGS. 1 and 1A, the network **8*a*, 8*b* of tubes 18 or other structures may be positioned directly within the barrel 36 of the syringe 14. In an alternative embodiment, the network 8 that is internal to a syringe 14 or other container 10 may also be housed in a network holder 22. In either embodiment, the barrel 36 of the syringe 14 may contain a propellant fluid 16 that, upon initiation of flow, provides pressure to release or eject the agent 12 from the network 8. The propellant fluid 16 need not be pre-filled in the barrel 36** of the syringe 14, but instead may be added to the barrel 36 of the syringe 14.

The sub-dividing volume structure of tubes 18 in the network 8 may assume a variety of geometries and configurations. As shown in FIGS. 1A, 2, 4A, 4B and 4C, the tubes 18 may be straight, coiled, helical, in random filaments 38, in an angular or stairstep (not shown) configuration, or may have other configurations. All of these alternatives are appropriate for use in any of the illustrated embodiments. The sub-dividing network 8 need not encompass tubes 18 at all; all shown in FIGS. 4A, 4B and 4C, the network 8d, 8e and 8f respectively, may be a series of discrete cells 42 (see FIG. 4B), or may have a sponge 44 type of structure (see FIG. 4A). In a cell 42 structure, the agent 12 is retained in or on discreet cells 42. In a sponge 44 structure, the agent 12 is either absorbed in or adsorbed on the sponge 44, rather than contained within tubes 18 or cells 42. A cell 42 or sponge 44 structure may also be used effectively in a network holder 22 separate from a syringe 14. In any embodiment, the network 8 may be configured so that there is a non-uniform direction for all sub-volumes, that is, there is no single upward, downward or lateral direction for all sub-volumes.

Figure 5:
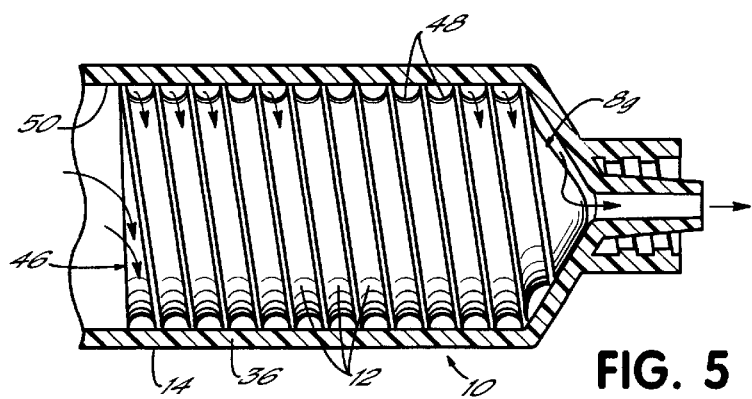
Figure 6:
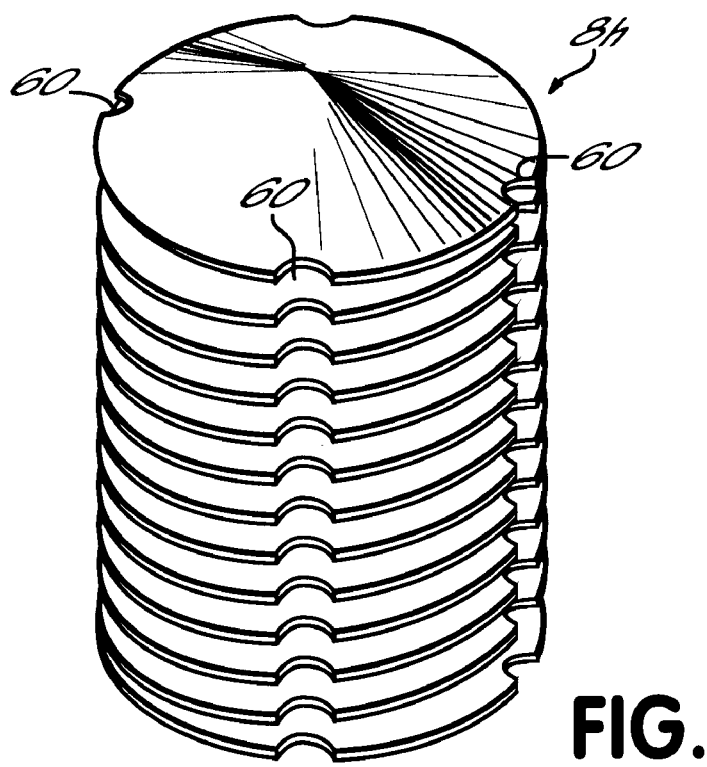

With reference to FIG. 5, a network 8g that is integral with the container 10 is shown. In this embodiment, the network 8g is fabricated as grooves or channels 48 that are etched or otherwise manufactured within the container 10 itself. For example, a syringe 14 may have a cylindrical plug 46 disposed in the barrel 36, where the plug 46 has parallel or spiral grooves 48 in its outer surface. The grooves 48 contain the agent 12 between the syringe 14 inner wall 50 and barrel 36. As shown in FIG. 6, the grooves 48 may contain substantially perpendicular channels 60 at one or more regularly spaced intervals. The channels 60 permit rapid and uniform filling of the network 8 with agent 12 added into one side of a container 10 when the other side of the container 10 is sealed. In another embodiment, the syringe 14 has a cylindrical plug 46 disposed in the barrel 36 as previously described, where the inner wall 50 of the syringe 14 has parallel or spiral grooves in its structure. The grooved structures 48 may also be used in a separate network holder 22. In these embodiments, the grooved structure 48 comprises the network 8 which sub-divides the volume of agent 12. It will thus be appreciated that the network 8 may assume a variety of forms and configurations whereby a volume of agent 12 can be sub-divided into smaller volumes with increased surface area of the agent 12 over which the propellant fluid 16 flows to reduce sedimentation.

The network 8, whether in the form of tubes 18, cells 42 or sponges 44, may be made of any biocompatable material that can withstand sterilization and is inert with respect to the agent 12, the propellant fluid 16, and the container 10. Examples of such materials for a tubular 18 network include biocompatible tubing such as polyethylene, polypropylene, silicon, rubber, etc., for example, Tygon® tubing (halogenated vinyl plastic, Norton Plastics). Tubes 18 used in kidney dialysis devices, such as cellulose tubes 18 having a nominal diameter of 200 µm, may also be used in the invention In a network 8e having cells or voids, the cells 42 may be produced by incomplete fusion of pieces of fusable material such as thermoplastics or metals. The cells 42 may be made of Delrin™, polycarbonate such as Lexan™, polyethylene, polypropylene, silicon, rubber, etc. In a network 8d having a sponge 44 structure, the sponge 44 may be made of porous Delrin™, porpous polycarbonate such as Lexan™, porous polyethylene, porous polypropylene, porous silicon, porous rubber, etc.

The size and volume of the network 8, container 10, and network holder 22 may vary, depending upon a number of factors. These factors include the volume of agent 12, the size of the container 10, the duration of the imaging or other procedure to be performed, etc. There is neither a maximum nor a minimum volume for the network 8, container 10, or network holder 22, and an exponential range of volumes is contemplated by the invention. For embodiments in which the network 8 is internal or integral with the container 10, however, the volume of agent 12 contained within the network 8 is at most one-half the volume of propellant fluid 16 in the container 10 This ensures that substantially all the agent 12 will be released from the network 8 by the flow of propellant fluid 16. For example, volumes of contrast agent 12 injected for enhanced ultrasound imaging may range from 1 ml to about 10 ml. As an example, a 3 ml volume of agent would require using about a 10 ml syringe 14, with the tubular 18 or other structure of the network 8 containing 3 ml agent 12 and the remaining volume of the syringe 14 containing at least 3 ml, and more typically 4–5 ml, of propellant fluid 16. A 3 ml volume of agent 12 may be sub-divided in a syringe 14 having ten threads or grooves 48 per inch, with the threads or grooves 48 one millimeter deep, each thread or groove 48 containing about 0.3 ml agent 12.

Figure 3:
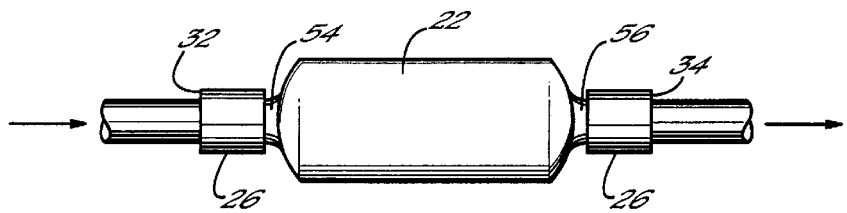
Figure 4A:
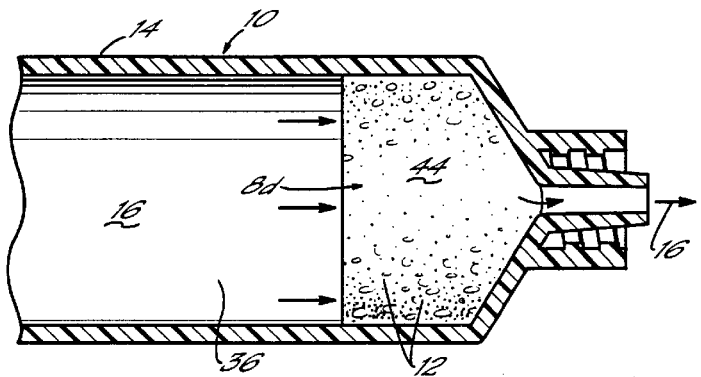
Figure 4B:
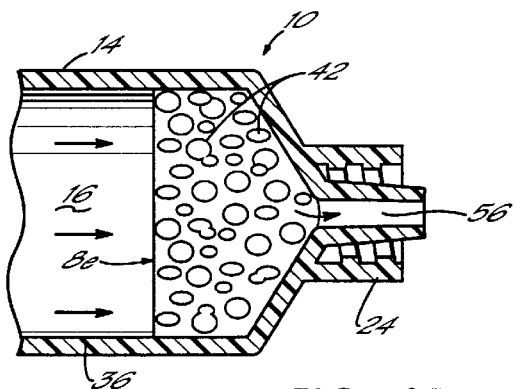
Figure 4C:
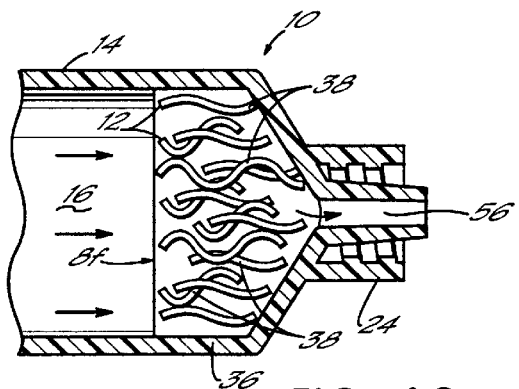

The container 10 and/or network holder 22 may be manufactured having the network 8 preloaded with a uniformly mixed suspension of agent 12 such as a pharmaceutical colloid. The container 10 and/or network holder 22 may have both an entry port 54 and an exit port 56 with appropriate fittings 26 such as luer locks for connection to standard tubing or catheters, as is known to one skilled in the art (FIG. 3). To eject the agent 12 in the network 8 from the exit port 56 of the container 10 or network holder 22 and into the patient through a patient connector line, propellant fluid 16 may be injected into the entry port 54 or, alternatively, pressure may be applied to the propellant fluid 16 already in the container 10. The container 10 may also have a single exit port 56 and a plunger 58, with liquid 60 in the opposite end, to permit use as a prefilled syringe (FIG. 1).

The specific location, position and configuration of the network 8 may depend upon an intended use. For example, an agent containing a gas other than air should be housed in a container 10 that has been purged of air. A container 10 made of glass may be rendered air-tight more easily than a plastic syringe, and thus is preferable for this agent. Likewise, a network 8 that is internal rather than external is preferred for use with an agent that contains a gas other than air. This allows the propellant fluid 16 to be purged of air and become saturated with the agent-containing gas, maintaining a substantially anaerobic environment prior to injection.

One advantage of the invention is that it eliminates the need for resuspension of agents 12 that may come out of suspension, either in their original container 10 or in a dose delivery container such as a syringe 14. Conventional containers 10 require mechanical devices or manipulations to maintain colloids such as a contrast agent 12 in suspension. By eliminating the need for prior resuspension of the agent 12 for single-bolus injection, the device and method of the present invention provides a competitive advantage for injectable agents 12. In accordance with the principles of the present invention, a syringe 14 having a network 8 containing agent 12 can remain resuspendable for more than five months.

Maintaining the agent 12 in a substantially fully resuspendable state assures consistent quality and reduced sensitivity to user technique. The agent 12 may be shipped already prepackaged in the network 8. This arrangement has the potential to reduce susceptibility of agents, such as microbubble preparations, to mechanical vibration and shock which may decrease the integrity of the agent 12. Dividing the volume of agent 12 into sub-volumes also allows it to be more quickly preheated to a desired temperature, facilitating the efficiency of the entire imaging procedure.

Another advantage of the invention is that the colloid or other agent 12 may be released, ejected or expelled from the exit port 56 of the container 10 by injecting a propellant fluid 16. This precludes the need to draw the pharmaceutical or contrast agent 12 into a syringe 14 for injection, and provides similar advantages as enjoyed by pre-filled syringes.

Figure 2:
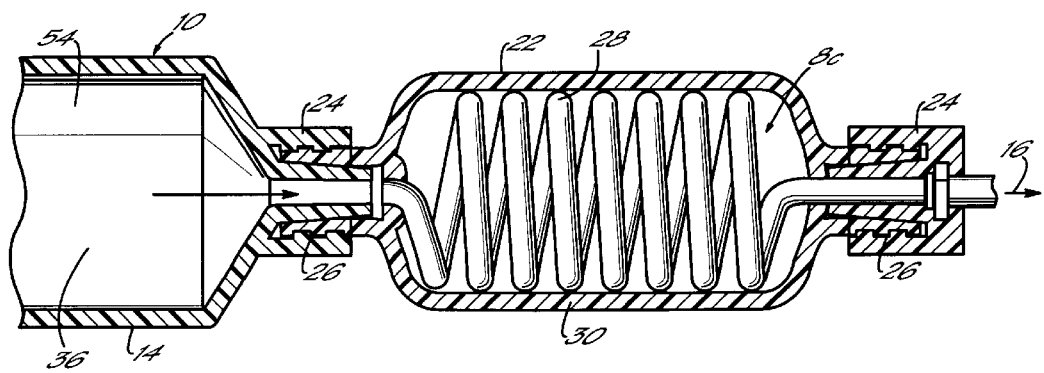

Still another advantage of the invention is that, in those embodiments such as FIGS. 2 and 3 where network 8 is external to the syringe 14, the exit port 56 of the dose delivery container 10 or network holder 22 may be connected to a short angiocatheter (not shown) that is very close to a venous or arterial puncture site in a patient. This arrangement prevents loss of suspension of agent 12 that would occur inside a longer catheter, and permits use of a manual or power syringe located a substantial distance away from the patient, while preventing the need for the agent 12 to maintain resuspendable in the manual or power syringe 14 and connecting tubing. Instead, the manual or power syringe and tubing need only contain a non-colloidal fluid that does not require mixing or resuspending during long injection times.

A further advantage of the invention is realized with an optional built-in plunger 58 in the syringe 14. A built-in plunger 58 permits use of the device as a manual syringe 14 or with a small, battery-operated power injector at the end of a very short angiocatheter. In either case, the filled syringe 14 could be located very close to a venous or arterial puncture site, precluding the need to maintain the agent 12 resuspended in a long catheter for infusion into a patient. This embodiment also precludes the need for a fluid-filled syringe 14 connected to the entry port 54 of the dose delivery container 10 in order to eject the agent 12 from the exit port 56 of the dose delivery container 10.

It should be understood that the embodiments of the present invention shown and described in the specification are exemplary embodiments contemplated by the inventor and are not limiting in any way. For example, the invention is not limited to use in the clinical area and may be used in research applications, as well as in other industries where uniformly suspended agents are needed, such as the food and beverage industries. In such cases, for example, the propellant fluids 16 may also include oils, epoxy resins, sugars, etc., depending upon the application. Therefore, various changes, modifications or alterations to these embodiments may be made or resorted to without departing from the spirit of the invention and the scope of the following claims.

What is claimed is:

1. A device for providing a volume of an agent with a propellant fluid, comprising:

a single syringe consisting of a side wall defining an interior space, an exit port, a plunger positioned in the interior space and having a sealing engagement with the side wall, the entire interior space between The plunger and the exit port containing the propellant fluid, and the plunger being movable in the interior space toward the exit port, and a helical tubular body defining a continuously open and uninterrupted fluid passageway within said interior space of said syringe, said helical tubular body being located between said plunger and said exit port and containing an agent, the fluid passageway having an outlet coupled in fluid communication with said exit port of said syringe and an inlet opening into said interior space, the inlet receiving propellant fluid when the plunger is moved so that the propellant fluid flows through said fluid passageway in direct contact with the agent and said outlet directing the agent contacted by the flow of the propellant fluid to said exit port.

2. The device of claim 1 wherein said agent is an imaging contrast agent.

3. The device of claim 1 wherein said agent is a microbubble preparation.

4. The device of claim 1 wherein said agent is a colloid.

5. The device of claim 1 wherein said propellant fluid is biocompatible.

6. The device of claim 1 wherein said passageway has a helical configuration.

7. A device for providing a volume of an agent with a propellant fluid, comprising:

only one syringe, said syringe having a side wail defining an interior space, an exit port, and a plunger positioned in the interior space and having a sealing engagement with the side wall, the entire interior space between the plunger and the exit port containing the propellant fluid, and the plunger being movable in the interior space toward the exit port, and a helical tubular body defining a continuously open and uninterrupted fluid passageway within said interior space of said syringe, said helical tubular body being located between said plunger and said exit port and containing the agent, the fluid passageway having an outlet coupled in fluid communication with said exit port of said syringe and an inlet opening into said interior space, the inlet receiving propellant fluid when the plunger is moved so that the propellant fluid flows through said fluid passageway in direct contact with the agent and said outlet directing the agent contacted by the flow of the propellant fluid to said exit port.

* * * * *

UNITED STATES PATENT AND TRADEMARK OFFICE
CERTIFICATE OF CORRECTION

PATENT NO. : 6,554,792 B2  Page 1 of 1
DATED : April 29, 2003
INVENTOR(S) : Hughes It is certified that error appears in the above-identified patent and that said Letters Patent is hereby corrected as shown below:

Column 6,
Line 11, "container 10 This ensures..." should be -- Container 10. This ensures --

Column 8,
Line 8, "between The plunger and..." should be -- between the plunger and... --

Column 8,
Line 35, "wail" should read -- wall --

Signed and Sealed this

Twenty-ninth Day of June, 2004

JON W. DUDAS
*Acting Director of the United States Patent and Trademark Office*